United States Patent [19]
Bormann et al.

[11] Patent Number: 5,262,162
[45] Date of Patent: Nov. 16, 1993

[54] CEREBRAL-ACTIVATING EXTRACT

[75] Inventors: Joachim Bormann, Göttingen; Lothar Demisch, Frankfurt am Main; Roman Gürtelmeyer, Mühltal; Rüdinger Koch, Frankfurt am Main; Wolfgang Schatton, Eschborn, all of Fed. Rep. of Germany

[73] Assignee: Merz & Co. GmbH & Co., Frankfurt am Main, Fed. Rep. of Germany

[21] Appl. No.: 755,814

[22] Filed: Sep. 6, 1991

[51] Int. Cl.$^5$ ............................................. A61K 35/78
[52] U.S. Cl. ................................................... 424/195.1
[58] Field of Search ..................................... 424/195.1

[56] References Cited

U.S. PATENT DOCUMENTS 4,703,060  10/1987  Traitler et al. ..................... 514/549

FOREIGN PATENT DOCUMENTS

| | | |
|---|---|---|
| 0092085 | 10/1983 | European Pat. Off. . |
| 0296751 | 12/1992 | European Pat. Off. . |
| BSM6760M | 3/1969 | France . |
| 2583640 | 12/1986 | France . |
| 2622453 | 5/1989 | France . |
| 0475233 | 8/1969 | Switzerland . |
| 1068609 | 5/1967 | United Kingdom . |
| 2147911 | 5/1985 | United Kingdom . |
| 2183635 | 6/1987 | United Kingdom . |

OTHER PUBLICATIONS

Chem. Abst., 109:72306w, 1988.
Chem. Abst., 110:3397t, 1989.
Chem. Abst., 111:95699g, 1989.
Chem. Abst., 112:34640e, 1990.
Drugs & Pharmacology 1989-1990 #20, 1 of 1, "Selegiline versus oxiracetam in patients with Alzheimer-type dementia", Falsaperla, et al. (Abstracting Clinther. 12/5, 376-384 (1990).
Drugs & Pharmacology 1991-Apr. 1992 #28, 1 of 8, "L-deprenyl therapy improves verbal memory in amnesic alzheimer patients", Finali, et al. (Abstracting Clinneuropharmacol 14/6 523-536 (1991).
Drugs & Pharmacology 1991-4/92 #28, 2 of 8, "The use of selegiline in Alzeimer's patients with behavior problems", Goad, et al. (Abstracting J-Clinpsychiatry, 52/8 342-345 (1991).
Drugs & Pharmacology 1991-Apr. 1992 #28, 3 of 8, "A pilot study of low-dose L-deprenyl in Alzheimer's disease", Schneider, et al. (Abstracting J-Geriatrpsychiatry-Neurol, 4/3, 143-148 (1991).
Drugs & Pharmacology 1989-1990 #28, 6 of 8, "Selegiline in the treatment of mild to moderate Alzheimer-type dementia", Monteverde, et al. (Abstracting Clin-Ther. 12/4, 315-322 (1990)).
Drugs & Pharmacology 1987-1988 #28, 8 of 8, "Cognitive effects of L-deprenyl in Alzheimer's disease", Tariot, et al. (Abstracting Psychopharmacology, 91/4, 489-495 (1987).
11 Mezz, 87212378, "L-deprenyl in Alzheimer's disease. Preliminary evidence for behavioral change with monoamine oxidase B inhibition", Tariot, et al. (Abstracting Arch-Gen-Psychiatry, 44(5), 427-433 (May 1987).
Psychopharmacologia (Berl.) 13, 222-257 (1988); Irwin, "Compressive Observational Assessment etc.".
Neuropsychobiology 18: 212-218 (1987), "Radioelectroencephalographic comparison of memantine with receptor-specific drugs acting on dopaminergic transmission in freely moving rats", Dimfel, et al.

(List continued on next page.)

Primary Examiner—John W. Rollins
Attorney, Agent, or Firm—Gordon W. Hueschen

[57] ABSTRACT

The use of an effective monoamine oxidase-inhibitory amount or portion of black currant juice (Ribes nigrum L.) or concentrate or dry extract thereof to activate the brain and central nervous system, in a living animal, especially a human being, in need thereof, and thereby to increase the general cerebral performance, especially in healthy and elderly people, and for the prevention, treatment, and alleviation of neurodegenerative diseases associated with reduced cerebral performance, such as Parkinson's disease, dementia, and mood disorders, and compositions thereof for such purpose, are disclosed.

15 Claims, No Drawings

OTHER PUBLICATIONS

Neurophychobiology 19: 116-120 (1988), "Monitoring of the effects of antidepressant drugs in the freely moving rat by radioelectroencephalography (tele-stero--EEG)", Dimpfel, et al.

13 Mezz, 81099269, "Deprenyl in Parkinson Disease", Eisler, et al. (Abstracting Neurology 31(1), 19-23 (Jan. 1981).

1 Mezz, "Deprenyl effects on levodopa pharmacodynamics, mood, and free radiaca scavenging", Baronti, et al. (Abstrcting Neurology 42 (3 Pt 1), 541-544 (Mar. 1992)).

Drugs & Pharmacology 1980-1981, #30, 2 of 2, "Antidepressant potentiation of 5-hydroxytryptophan by L-Deprenil in affective illness" (Abstracting J-Affect-Disord. 2/2, 137-146 (1980)).

Acta Neurologica Scandinavica, No. 136, vol. 84, 1991, "New approaches to the treatment of early Parkinson's disease", U. K. Rinne, et al., pp. 70, 73, 79, 87.

Meth and Find Exptl Clin Pharmacol 1987; 9(6): 385-408; "Topographic brain mapping of EEG in neuropsychopharmacology—Part II. Clinical applications" (Pharmaco EEG Imaging), Saletu, et al.

Z.EEG-EMG 12 (1981) 21-32, "Beispiele für die Projektiovon Substanzwirkungen typischer Psychopharmaka auf eine elektriphysiologische MeBebene", Hermann, et al.

Human Psychopharmacology Measures and Methods, vol. 1, Edited by I. Hindmarch and P. D. Stonier, A Wiley Medical Publication, 1986, pp. 176-179 and 184 (B. Saletu, "The Use of Pharmaco-EEG in Drug Profiling").

J. Ment. Sci. (1960), "Drugs and Personality", VIII. The effects of stimulant and depressant drugs on visual after-effects of a rotating spiral, Eysenck, et al., pp. 842-844.

Perception & Psychophysics, 1987, 41 (1), 17-22, "Interaction of signal discriminability and task type in vigilance decrement," Parsuraman, et al., Copyright 1987 Psychonomic Society, Inc.

Elsevier, 1988, "Comparative Evaulation of Rating Scales for Clinical Psychopharmacology", van Riezen, et al., pp. 78-79.

Martindale, "The extra pharmacopoeia", London, The Pharmaceutical Press 1255 and 1257 (1989).

Martindale, "The extra pharmacopoeia", London, The Pharmaceutical Press 1255 and 1257 (1989).

EPO Search Report EP 92308063 dated Dec. 15, 1992.

Armstrong, "Recent Trends in Research and Treatment of Parkinson's Disease", SCRIP pp. 58-61 and 63-67 (May 1989).

CEREBRAL-ACTIVATING EXTRACT

BACKGROUND OF THE INVENTION AND PRIOR ART

1. A Field of Invention

The use of black currant juice (Ribes nigrum L.) or black currant juice concentrate or dry extract thereof, to inhibit monoamine oxidase and to activate the brain and central nervous system, in a living animal, especially a human being, in need thereof, and thereby to increase the general cerebral performance, especially in healthy and elderly people, and for the prevention, treatment, and alleviation of neurodegenerative diseases associated with reduced cerebral performance, such as Parkinson's disease, dementia, and mood disorders, and compositions thereof for such purpose.

2. Background of the Invention and Prior Art

The neurotransmitter dopamine is one of the most essential cerebral neurotransmitters responsible for the modulation of cerebral performance.

Reduced dopamine concentrations, which are often present in elderly people and specific neurodegenerative diseases, are always associated with reduced cerebral function.

Unfortunately, the substitution of dopamine (which is the main target of L-dopa therapy) does not have the desired effect, since dopamine substitution supports the decay of dopaminergic neurons, thereby accelerating the loss in cerebral function.

As neuronal decay is also supported by biotransformation products of dopamine, treatment with dopamine metabolism inhibitors should be preferred.

One of the first steps of dopamine degradation is catalyzed through monoamine oxidases, the inhibition of which is one aim of any therapeutic intervention addressed thereto.

Within the framework of an extensive pharmacognostic screening of various plants and the extracts thereof, it has been found unexpectedly that the juice of black currant has monoamine oxidase (MAO)-inhibiting properties and a cerebro-activating effect.

In the patent literature, the black currant has already been mentioned in connection with an enhancement of cerebral performance (EPA 88305450.4; EP 0296751 A1). In contrast to the present invention, however, in this patent application the desired enhancement effect is directly ascribed to the kernel oil and the unsaturated essential fatty acids (e.g., gamma linolenic acid). Within the scope of the investigations relating to the present invention, however, it was demonstrated that the juice of black currant and its concentrates and dry extracts, which are employed according to the present invention, contain essentially no or only insignificant amounts of kernel oil or unsaturated fatty acids ($C_{18}$, w3, 6, 9=0.02% and $C_{18}$, w3, 6=0.0018% by weight), so that such materials do not contribute to the excellent MAO-inhibiting and cerebro-stimulating activities of the black currant juice according to the present invention.

On the contrary, it was demonstrated that black currant juice and concentrates and dry extracts thereof are characterized by MAO-inhibiting and cerebro-activating effects. According to these properties, black currant juice has the characteristic of enhancing cerebral performance in healthy and elderly people, and in patients suffering from neurodegenerative diseases, especially since it is believed that MAO-B inhibitors can halt the progression of such diseases, e.g., Parkinson's disease, for example, by preventing further degeneration of dopaminergic neurons. For details, *inter alia*, see SCRIP, May 1989, "Recent Trends in Research and the Treatment of Parkinson's Disease" by Professor William Armstrong (PJB Publications Ltd), cover sheet plus pages 58-61 and 63-67, in support of this relationship and the nexus between MAO-B inhibitory activity of a compound and its utility in the alleviation of neurodegenerative diseases associated with reduced cerebral performance.

Such desirable results have been substantiated by different test systems:

1. Demonstration of MAO-inhibiting action in vitro
2. Demonstration of MAO-inhibiting action in humans
3. Demonstration of stimulating effect in the mouse
4. Demonstration of cerebro-activating effect in the rat
5. Demonstration of cerebro-activating effect in humans all as shown hereinafter under Pharmacological and Clinical Results.

OBJECTS OF THE INVENTION

It is an object of the present invention to provide a novel composition and method for the inhibition of monoamine oxidase, activation of the brain and central nervous system, and thereby to increase the general cerebral performance, especially in healthy and elderly people, as well as for the prevention, treatment, and alleviation of neurodegenerative diseases associated with reduced cerebral performance, such as Parkinson's disease, dementia, and mood disorders. A further object of the invention is to provide such method and composition which involves the use of an effective amount of black currant juice (Ribes nigrum L.) or concentrate or dry extract thereof, or the pharmaceutically-effective fraction of any of the foregoing, for such purpose. Another object of the invention is to provide such method and composition which involves the employment of a pharmaceutically or orally-acceptable carrier or diluent together with the black currant juice or concentrate or dry extract thereof to facilitate the oral administration of such a composition. Still a further object of the invention is to provide such a composition and method in which the composition is in the form of a pharmaceutical, food, or dietetic food composition and the diluent or carrier is adapted for the particular type of composition, especially such a composition in the form of a tablet, a coated tablet, a syrup, a tonic, or a drink mix. An additional object of the invention is the provision of such a method and composition wherein the amount of the black currant juice, concentrate, or dry extract is present or employed in an amount between about 10 mg and 10 g per unit dosage form, preferably between about 100 mg and 5 g per unit dosage form, and wherein the black currant juice, concentrate, or dry extract is administered in an amount between about 100 mg and 50 g per day, preferably between about 1 and 20 grams per day. Still an additional object is the provision of such a method and composition wherein the black currant juice is present in the form of an at least 2-fold concentrate thereof, preferably and approximately 4-fold to 8-fold concentrate thereof, and most especially an approximately 5.5-fold concentrate thereof, or in the form of a dry extract thereof. Further objects of the invention will become apparent hereinafter, and still other objects of the invention will be apparent to one skilled in the art.

SUMMARY OF THE INVENTION

What we claim to be our invention, therefore, comprises *inter alia*, alone or in combination, the following:

A method for the inhibition of monoamine oxidase, increase of cerebral performance, improvement in the state of mood, and the prevention and treatment of neurodegenerative diseases in a living human in need thereof, comprising the step of orally administering to such human an effective monoamine oxidase-inhibitory and cerebro-activating portion or amount of black currant juice or concentrate or dry extract thereof; such a method wherein the black currant juice or concentrate or dry extract thereof is administered in an amount between about 100 mg and 50 g per day; such a method wherein the black currant juice or concentrate or dry extract thereof is administered in an amount between about 1 and 20 grams per day; such a method wherein the black currant juice or concentrate or dry extract thereof is orally administered in the form of a composition wherein it is present together with a pharmaceutically- or orally-acceptable carrier or diluent; such a method wherein the black currant juice is in the form of an at least two-fold concentrate, preferably an approximately four-fold to eight-fold concentrate thereof; such a method wherein the black currant juice is in the form of an approximately 5.5-fold concentrate thereof; and such a method wherein the black currant juice is in the form of a dry extract thereof.

Moveover, an orally-administrable composition, suitable for oral administration to a living human, thereby to inhibit monoamine oxidase, increase cerebral performance, improve the state of mood, and assist in the prevention and treatment of neurodegenerative diseases, comprising an effective monoamine oxidase-inhibitory portion or amount of black currant juice or concentrate or dry extract thereof, together with a pharmaceutically- or orally-acceptable diluent or carrier; such a composition wherein the composition is in the form of a pharmaceutical, food, or dietetic food composition and the diluent or carrier is adapted for the particular type of composition; such a composition wherein the composition is in the form of a tablet, a coated tablet, a syrup, a tonic, or a drink mix; such a composition in unit dosage form wherein the black currant juice or concentrate or dry extract thereof is present in an amount between about 10 mg and 10 g per unit dosage form; such a composition wherein the black currant juice or concentrate or dry extract thereof is present in an amount between about 100 mg and 5 g per unit dosage form; such a composition wherein the black currant juice is present in the form of an at least two-fold concentrate thereof, preferably an approximately four-fold to eight-fold concentrate thereof; such a composition wherein the black currant juice is in the form of an approximately 5.5-fold concentrate thereof; and such a composition wherein the black currant juice is in the form of a dry extract thereof.

PHARMACOLOGICAL AND CLINICAL RESULTS

The following pharmacological and clinical evaluations and results are given to illustrate the method or use aspect of the invention, but are not to be construed as limiting.

Test 1—Demonstration of MAO-Inhibiting Action In Vitro

The test was carried out using a concentrate of black currant juice in 5.5-fold concentration. After adjustment of the pH to 7.2, one aliquot (40 $\mu$l) was pre-incubated with the enzyme (1 mg mitochondrial protein, rat liver) for 20 minutes at room temperature. For determination of monoamine oxidase (MAO) type A and B activity, the reaction was started by adding 50 nmol $^{14}$C benzylamine or $^{14}$C serotonin. After one minute of incubation in a shaking water bath (37° C.), the reaction was stopped (1 ml perchloric acid, 0.5M), the acidic and neutral deaminated products being determined after separation by ion-exchange chromatography.

The effect of the juice concentrate is described in percent of inhibition, related to a similarly-incubated buffer control.

Result

The black currant concentrate effects a 61% inhibition of MAO type B, and an 37% inhibition of MAO type A.

Test 2—Demonstration of MAO-Inhibiting Action in Humans

In a test in humans, three healthy subjects received 5, 20, and 50 g of a concentrate of black currant juice in 5.5-fold concentration by the oral route. Blood samples were taken at times—15, 0, 30, 60 and 180 minutes. After centrifugation, platelet-rich plasma was obtained, the MAO type B activity in thrombocytes being determined by a method similar to that described for Test 1.

Result

MAO type B activity is inhibited in all three subjects with dependency upon dosage and time.

Maximum inhibition is obtained 60 minutes after application, and is between 70 and 90% at optimum dosage of 20 grams. This result was confirmed by 92% inhibition in the controlled test as specified under Test 5, using 50 g juice concentrate.

Test 3—Demonstration of Stimulating Effect in the Mouse

Five mice each received 40, 120, 360, 1080 and 3240 mg/kg of pH-neutralized black currant juice in 5.5-fold concentration by oral intubation. Acute mortality was not observed. Nineteen behavioral and performance parameters were scored 40 minutes after application.

Result

Significant changes in behavior were found only for the parameter (8) defined as "excitation" or "excitement", scoring 24 out of a possible 25 at all doses, especially of 360 mg/kg and above.

This shows that even low doses of black currant juice effect a considerable cerebral stimulation in mice.

Test Details—Introduction

The purpose of the study was to test the CNS activity of the black currant juice concentrate, following its p. o. application to mice. A battery of 19 tests was employed to investigate the effects of the drugs on toxic, behavioral and motor performance parameters.

Methods

The test material was suspended in physiological saline supplemented with 1% methylcellulose and 1% Tween 80 TM. The test included 15 mice with 5 animals in each dosage group (360, 1080, and 3240 mg/kg).

The test material was administered by gavage to female NMRI mice weighing approximately 20 g. Pharmacological testing was performed 40 minutes after the application. Mortality was observed at 1 hour and 24 hours.

The test parameters included:

| | |
|---|---|
| 1. | 1 h-mortality |
| 2. | 24 h-mortality |
| 3. | Tremors |
| 4. | Tonic convulsions |
| 5. | Clonic convulsions |
| 6. | Ptosis |
| 7. | Sedation |
| 8. | Excitement |
| 9. | Loss of exploratory activity |
| 10. | Loss of pinna reflex |
| 11. | Loss of righting reflex |
| 12. | Mydriasis |
| 13. | Catalepsy |
| 14. | Loss of bar grasp |
| 15. | Rotarod test (1 min) |
| 16. | Rotarod test (2 min) |
| 17. | Analgesia |
| 18. | Electroshock protection |
| 19. | Post-electroshock mortality |

The total number of responding mice was determined for each parameter.

Results

The pharmacological profile at all dosages was determined. Distinct effects (Score>10) were observed for all dosage levels only with respect to excitement (8). All doses of 360 mg/kg or above were equally effective (Score 24).

Also, irrespective of the dose, only moderate effects on rotarod performance (2 min) and on post-electroshock-induced mortality were observed (Score 6–7).

Comparable distinct effects were also observed when using a pharmaceutically-effective subfraction of black currant juice (e.g., prepared by means of an ethanolic or $CO_2$-extraction procedure).

Test 4—Demonstration of Cerebro-Activating Effect in the Rat

A pharmaco-EEG was recorded to assess the cerebro-activating effect in rats. For this purpose four (4) bipolar concentric electrodes with microplug were placed on a base plate and implanted in rats with reverse day/night rhythm. The plug was used for a 4-channel transmitter for telemetric transmission of the field potentials from frontal cortex, hippocampus, striatum, and reticular formation. The signals were subjected to Fast-Fourier-Transformation, and the mean values were determined for the density spectra within 15 minutes.

By dividing the spectra into 6 different frequency ranges, i.e., delta, theta, alpha 1, alpha 2, beta 1 and beta 2 (1.25–35 Hz), pharmaco-specific changes could be assessed in relation to the values obtained before application. The animals received a 5.5-fold concentration of black currant juice in doses of 1.5, 3 and 6 ml/kg. The effects were determined over a period of 4 hours.

Result

After application of the concentrate, the main change observed was a considerable decrease in the delta and alpha 2-band, as compared to a lesser decrease in the alpha 1-band.

There is great correspondence between frontal cortex and striatum. In the hippocampus the reduction in the alpha-2 band is less pronounced, whereas there is almost no decrease in the delta band for the reticular formation. The relation between the changes is almost identical in all four brain areas, and very stable.

The action sets in at 1.5 ml/kg, reaching its maximum already at 3 ml/kg.

From these findings it can be seen that black currant juice has a pronounced effect on dopaminergic transmission. As to the expected clinical efficacy, a stimulating and mood-elevating effect is indicated.

Test 5—Demonstration of Cerebro-Activating Effect in Humans

In a single-blind controlled study the pharmaco-EEG, duration of spiral after-effect (SAE), profile of mood state (POMS), MAO activity (cf. 2), and blood pressure were assessed after the administration of 50 g black currant juice concentrate (5.5-fold) in comparison with orange juice as placebo.

As comprehensive measurements are required, the study was carried out on only a single person.

The bipolar EEG is registered by paracentral longitudinal leads. From the pharmaco-EEG the spectra are calculated using the Fast-Fourier-Transformation. The spectrum is divided into band ranges from delta to beta 2 (0.25–31.75 Hz). The cerebral activity is determined from the changes in spectral power in the individual frequency bands.

The SAE test is used to assess central nervous excitability. The subject is stimulated by rotation of a so-called Archimedean spiral. After the spiral has stopped, the test person experiences a movement after-effect, the duration of which serves as a measure for the central excitation effect.

The POMS test is a self-rating scale. The values for the four emotional states, namely, depression, fatigue, lack of drive, and bad moods (mood level) are determined from the subject's self-ratings of the individual emotional states.

The test was carried out over a period of three days with administration and measurement at the same time each day:

Day 1 = Baseline—no administration
Day 2 = Administration of test material
Day 3 = Administration of placebo

Result

MAO type B activity in thrombocytes was inhibited to the extent of 92%, as stated under Test 2. As compared to control and baseline values, an increase of delta and a reduction of alpha 1 and alpha 2 was observed 60 minutes after the application of the test material.

A few minutes before that time, a prolongation of SAE duration, a striking reduction of "fatigue", and a stronger increase in "drive" was observed in comparison with the two other test days (1 and 3).

There was no significant influence of the test material on blood pressure.

These findings underline the results obtained in the animal experiments showing a central nervous activation by black currant juice.

In a further study in humans employing a drink containing concentrated black currant juice, in each case containing definitive quantities of the juice concentrate, and comparing the test materials with a drink containing no black currant juice, but otherwise the same in constitution, the black currant juice concentrate was found to have a definite effect on mental performance and vigilance. Test details follow:

The effects of 3.4 g and 10.2 g HB-1 (black currant juice concentrate, 5.5 fold) on visual perception, concentration, vigilance, psychomotor performance, state of mood and general tolerance was tested in n=24 healthy young volunteers (8 subjects (Ss) each group). The whole experiment lasted 5 days, with the first day as an exercise day. On the following days (experimental days 1–4) the Ss received either Placebo or 3.4 or 10.2 g HB-1 at 1:30 P.M.

On each day the Ss ran through a test battery five times per day. The test battery consisted of the following psychological tests or scales:

Spiral After Effect (SAE)
Posner—Comparison of digits (POSNER)
Tracking performance test (TRACKING)
Vigilance test—Modified version of the test published by Parasuraman, Raja and Mouloua, Mustapha: Interaction of signal discriminability and task type in vigilance decrement. In: Perception & Psychophysics 41 (1), 17–22 (1987).
Profile of Mood States (POMS)
List of Bodily Symptoms (LBS)
Blood Pressure (BP sys. and BP diast.) and Heart Frequency (HF).

Additionally the quality of sleep and related sleep factors were assessed by means of a sleep questionnaire (SF-A) at the beginning of each experimental day.

The sessions started at 10:00 A.M. and were finished in the evening at 5:15 P.M. The sessions 1 and 2 in the morning were used as warming up sessions. The effect of HB-1 was evaluated by means of the test data of sessions 3–5.

Effects related to HB-1 were seen with POMS, POSNER and Vigilance test. The results show that HB-1, mainly in the dose of 10.2 g, has an effect on mental performance and vigilance. SAE and tracking performance were not found to be significantly influenced by HB-1 in this particular evaluation.

The tolerance of HB-1 was very good. The results of LBS showed no significant differences between the treatment groups.

Compositions, Especially Galenical Preparations Comprising the Active Ingredient Together with a Pharmaceutically- or Orally-Acceptable Diluent or Carrier.

The juice of black currant according to the invention can be used as such but is preferably employed in the form of an aqueous concentrate thereof. Any concentration is advantageous, and a concentration of at least twofold, preferably between about fourfold and eightfold, is preferred, with a concentration of about 5.5 fold being especially convenient and preferred. Also preferred is an extract, i.e., a dry extract thereof, such as is readily obtained by lyophilization, spray drying, or forcing the juice under pressure through a cannula, syringe, or venturi. By addition of suitable diluents to the juice, concentrate, or to the dry extract, readily-flowable fluids are obtained.

These basic materials are suitable for incorporation into many galenical presentation forms for use as drugs, foods, and dietetics.

As to pharmaceutical preparations, liquid (syrup) and solid presentation forms (tablets, and especially film-coated tablets) are representative. Dietetic preparations can representatively comprise liquid presentation forms (e.g., aqueous/alcoholic), instant drinks (e.g., dry granulate), and effervescent tablets.

The following Examples are given to illustrate the compositions of the invention, but are not to be construed as limiting.

EXAMPLE 1

Dry black currant juice or concentrate, preferably a 5.5-fold concentrate, under vacuum, add a suitable carrier (e.g., maltodextrin), and prepare a readily-flowable dry extract. Mix the extract in a dosage of, e.g., 500 mg per tablet, with a suitable adjuvant, e.g., lactose, microcrystalline cellulose, starch, highly-dispersed silicon dioxide (possibly hydrated), magnesium stearate, or the like, granulate moisture-free and compress into tablets on a suitable tabletting machine. Due to the hydrophilic character of the extract, provide the tablets with a conventional outer protective coating, and fill into blister packs.

EXAMPLE 2

Multivitamin Syrup with Black Currant Juice Concentrate

| | |
|---|---|
| Black currant juice concentrate (5.5-fold) | 10.0 g |
| Vitamin $B_1$ hydrochloride | 2.0 mg |
| Vitamin $B_2$ phosphoric acid ester phosphate Sodium Salt | 1.5 mg |
| Vitamin $B_6$ hydrochloride | 1.5 mg |
| Nicotinamide | 20.0 mg |
| Vitamin C | 50.0 mg |
| D-panthenol | 10.0 mg |
| Sugar | 40.0 g |
| Glycerol | 5.0 g |
| Sorbic Acid | 50.0 mg |
| Flavors | q.s. |
| Distilled Water | q.s. ad. ml 100.0 |

Dissolve the sugar in water, and add the vitamins to the sugar solution. Dissolve sorbic acid in glycerol, and add to the sugar solution. Finally, add the black currant concentrate and the flavors. Filter the solution and fill into 100-ml bottles.

EXAMPLE 3

Tonic with Black Currant Juice Concentrate

| | |
|---|---|
| Black currant juice concentrate (5.5-fold) | 20.0 g |
| Sugar | 15.0 g |
| Glucose syrup | 15.0 g |
| Sugar dye | 1.0 g |
| Ethanol | 12.0 g |
| Flavors | q.s. |

-continued

| Distilled Water | q.s. ad ml 100.0 |
|---|---|

Dissolve sugar, syrup and sugar dye in water. Add ethanol, black currant juice concentrate and the flavors. Filter the solution and fill into 100-ml bottles.

EXAMPLE 4

Instant Drink (Dry Granulate)

| I. | Black currant dry extract | 1500.0 mg |
|---|---|---|
| | Boeson VP* | 100.0 mg |
| | Flavors | 100.0 mg |
| | Sucrose | 8600.0 mg |
| II. | Ethanol | about 5.0 ml |
| | Methyl cellulose | 200.0 ml |

*Boesen VP (TM; Boehringer Ingelheim) is a neutral glyceride mixture used as an antiagglomerating and lubricating agent.

Pass mixture I through a 1-mm screen and granulate with solution II. Dry in a drying chamber until the odor of ethanol is no longer apparent. Shake 10 g of the granulate with 100 ml of water to prepare the ready-to-use suspension.

EXAMPLE 5

Multivitamin-Concentrate with Black Currant Juice Concentrate

| 1. | Acerola*-Cherry-Concentrate | 1.20 g |
|---|---|---|
| 2. | Black Currant Juice Concentrate (5.5-fold) | 3.40 g |
| 3. | Gelee Royal** | 0.25 g |
| 4. | Mate***-Liquid-Extract (50 Vol. % Ethanol) (15-20 mg Caffeine + Theobromine) | 1.76 g |
| 5. | Guaranae****-Dry Extract 6.5:1 (30-40 mg Caffeine + Theobromine) | 1.70 g |
| 6. | Vitamins: | |
| | Vitamin B1 Nitrate | 2.34 mg |
| | Vitamin B2 | 3.36 mg |
| | Vitamin B6 Hydrochloride | 3.21 mg |
| | Vitamin B12 | $7.5 \times 10^{-3}$ mg |
| | Biotin | $150.0 \times 10^{-3}$ mg |
| | Folic Acid | $240.0 \times 10^{-3}$ mg |
| | Nicotinic acid amide | 25.20 mg |
| | Calcium Pantothenate | 12.00 mg |
| | Vitamin C | 75.00 mg |
| | Vitamin E Acetate | 19.80 mg |
| 7. | Magnesium Gluconate (equivalent to 100 mg Mg ion) | 1.80 g |
| 8. | Dextrose | 4.00 g |
| 9. | Grape Concentrate | 4.00 g |
| 10. | Malt Extract | 1.20 g |
| 11. | Flavors | q.s. |
| 12. | Water | q.s ad 40.00 ml |

* = Vitamin C rich West-Indian cherry of special breed
** = Royal jelly (food of bees given to immature bees in order to have them developed into a fertile queen) - used as a tonicity enhancer
*** = Extract from leaves from the Paraguayan mate (tea) tree for supplying caffeine, etc.
**** = Extract from the seeds of a Brazilian plant used in refreshment drinks for supplying caffeine, etc.

Manufacturing Procedure

Acerola Cherry-Concentrate, black currant juice concentrate and Maté-Extract are placed into a stirrer vessel.

Gelée Royal, Guaranae dry extract, and Vitamins B and C, dissolved in water, are added and mixed in.

Dextrose, grape-concentrate, malt extract and flavors are stirred in.

Vitamin E acetate, dispersed in a small amount of hot water, is added together with the rest of the water and mixed thoroughly.

After a filtration, the concentration is pasteurized in a suitable manner and filled into bottles.

It is thus seen that a method for the inhibition of monoamine oxidase and cerebral activation in a living animal, especially a human being, thereby to increase cerebral performance and assist in the prevention and treatment of neurogenerative diseases, has been provided, involving the oral administration of the natural product black currant juice or a concentrate or dry extract thereof as the active component or ingredient, as well as pharmaceutical, food, or dietary compositions embodying such active component, the amount of the said active component provided in any case being an effective monoamine oxidase-inhibitory and cerebro-activating amount, as well as novel unit dosage forms, especially solid or relatively concentrated dosage forms, of such compositions.

Various modifications and equivalents will be apparent to one skilled in the art and may be made in the compositions, methods, and procedures of the present invention without departing from the spirit or scope thereof, and it is therefore to be understood that the invention is to be limited only by the full scope which can be legally attributed to the appended claims.

We claim:

1. A method for the inhibition of monoamine oxidase, increase of cerebral performance, improvement in the state of mood, and the prevention and treatment of neurodegenerative diseases in a living human in need thereof, comprising the step of orally administering to such human a pharmaceutical composition consisting essentially of an effective monoamine oxidase-inhibitory and cerebro-activating portion or amount of black currant juice or concentrate or dry extract thereof which is essentially free of kernel oil and unsaturated fatty acids.

2. The method of claim 1 wherein the black currant juice or concentrate or dry extract thereof is administered in an amount between about 100 mg and 50 g per day.

3. The method of claim 2 wherein the black currant juice or concentrate or dry extract thereof is administered in an amount between about 1 and 20 grams per day.

4. The method of any of claims 1, 2, and 3, wherein the black currant juice or concentrate or dry extract thereof is orally administered in the form of a composition wherein it is present together with a pharmaceutically- or orally-acceptable carrier or diluent.

5. The method of any of claims 1, 2, and 3, wherein the black currant juice is in the form of an at least two-fold concentrate thereof.

6. The method of claim 5, wherein the black currant juice is in the form of an approximately fourfold to eightfold concentrate thereof.

7. The method of claim 5, wherein the black currant juice is in the form of an approximately 5.5-fold concentrate thereof.

8. The method of claim 5, wherein the black currant juice is in the form of a dry extract thereof.

9. An orally-administrable composition, suitable for oral administration to a living human, thereby to inhibit monoamine oxidase, increase cerebral performance, improve the state of mood, and assist in the prevention and treatment of neurodegenerative diseases, consisting essentially of an effective monoamine oxidase-inhibitory and cerebro-activating portion or amount of black currant juice or concentrate or dry extract thereof which is essentially free of kernel oil and unsaturated fatty acids, together with a pharmaceutically- or orally-acceptable diluent or carrier, wherein said composition is in the form of a tablet, a coated tablet, a multivitamin preparation, an alcohol-containing tonic, a dry granulate, an effervescent tablet, or an instant drink mix.

10. The composition of claim 9, in unit dosage form wherein the black currant juice or concentrate or dry extract thereof is present in an amount between about 10 mg and 10 g per unit dosage form.

11. The composition of claim 10, wherein the black currant juice or concentrate or dry extract thereof is present in an amount between about 100 mg and 5 g per unit dosage form.

12. The composition of claim 9, 10 or 11, wherein the black currant juice is present in the form of an at least two-fold concentrate thereof.

13. The composition of claim 12, wherein the black currant juice is in the form of an approximately fourfold to eightfold concentrate thereof.

14. The composition of claim 12, wherein the black currant juice is in the form of an approximately 5.5-fold concentrate thereof.

15. The composition of claim 12, wherein the black currant juice is in the form of a dry extract thereof.

* * * * *

UNITED STATES PATENT AND TRADEMARK OFFICE
CERTIFICATE OF CORRECTION

PATENT NO. : 5,262,162                                Page 1 of 2
DATED      : Nov. 16, 1993
INVENTOR(S) : Joachim Bormann, Lothar Demisch, Roman
              Gurtelmeyer, Rudiger Koch, Wolfgang Schatton It is certified that error appears in the above-indentified patent and that said Letters Patent is hereby corrected as shown below:

Title Page, [75]; Iventors:, third line "Rüdinger" should read
     -- Rüdiger --.
Title Page, OTHER PUBLICATIONS, column 2, line 21; "(1988)"
     should read -- 1968 --.
Title Page, OTHER PUBLICATIONS, column 2, line 22;
     ""Compressive"" should read -- "Comprehensive" --.

Title Page, OTHER PUBLICATIONS, page 2, column 1, approximately
     line 3;  "Neurophychobiology" should read
     -- Neuropsychobiology --.
Title Page, OTHER PUBLICATIONS, page 2, column 1, approximately
     line 11; "radiaca" should read -- radical --.

Title Page, OTHER PUBLICATIONS, page 2, column 1, approximately
     line 25,26; "Pro-jektiovon" should read
     -- Projektion von--.
Title Page, OTHER PUBLICATIONS, page 2, column 2, approximately
     line 1; "elektriphysiologische" should read
     -- elektrophysiologische --.
Title Page, OTHER PUBLICATIONS, page 2, column 2, the fourth
     line from the end; "92308063" should read -- 92308053 --.
Column 8, approximately line 36; "EXAMPLE2" should read
     -- EXAMPLE 2 --.

UNITED STATES PATENT AND TRADEMARK OFFICE
CERTIFICATE OF CORRECTION

PATENT NO. : 5,262,162

DATED : Nov. 16, 1993

INVENTOR(S) : Joachim Bormann, Lothar Demisch, Roman Gurtelmyer, Rudiger Koch, Wolfgang Schatton It is certified that error appears in the above-identified patent and that said Letters Patent is hereby corrected as shown below:

Column 9, line 2, 3' "q.s. ad ml
                    100.0"
should read --q.s. ad    100.0 ml--.

Column 10, line 4; "concentration" should read --concentrate--.

Signed and Sealed this

Seventeenth Day of May, 1994

BRUCE LEHMAN

Attest:

Attesting Officer         Commissioner of Patents and Trademarks

UNITED STATES PATENT AND TRADEMARK OFFICE
CERTIFICATE OF CORRECTION

PATENT NO. : 5,262,162
DATED : November 16, 1993
INVENTOR(S) : Joachim Bormann, Lothar Demisch, Roman Gortelmeyer, Rudiger Koch and Wolfgang Schatton It is certified that error appears in the above-indentified patent and that said Letters Patent is hereby corrected as shown below:

Title Page, [75] Inventors:, line 3; "Gurtelmeyer" should read -- Gortelmeyer --. (Declaration)

Title Page, [73] Assignee:; "Merz & Co." should read -- Merz + Co. --. (Assignment - Reel 5863, frame 610)

Title Page, under OTHER PUBLICATIONS,
Col. 1, line 7; "Clinther" should read -- Clin-Ther --.
line 12; "Clinneuropharmacol" should read -- Clin-Neuropharmacol --.
Col. 2, line 1; "Alzeimer's" should read -- Alzheimer's --
line 2; "J-Clinpsychiatry" should read -- J-Clin-Psychiatry --.
lines 6 & 7; "J-Geriatrpsychiatry-Neurol" should read -- J-Geriatr-Psychiatry-Neurol --.
line 26; "Dimfel" should read -- Dimpfel --.

UNITED STATES PATENT AND TRADEMARK OFFICE
CERTIFICATE OF CORRECTION

PATENT NO. : 5,262,162
DATED : November 16, 1993
INVENTOR(S) : Joachim Bormann, Lothar Demisch, Roman Gortelmeyer, Rudiger Koch and Wolfgang Schatton It is certified that error appears in the above-indentified patent and that said Letters Patent is hereby corrected as shown below:

```
Title Page (page 2), under OTHER PUBLICATIONS,
     Col. 1, line 5; "tele-stero-" should read
              -- tele-stereo- --.
            line 12; "Abstrcting" should read
              -- Abstracting --.
     Col. 2, line 1; "McBebene" should read
              -- Messebene --.
            line 14; "Parsuraman" should read
              -- Parasuraman --.
            line 16; "Evaulation" should read
              -- Evaluation --.
            lines 21 & 22; delete these repeated lines
            "Martindale, . . . . . . . (1989)."
     Col. 1, line 6; delete "A".
     Col. 4, line 31; "an" should read -- a --.
```

Signed and Sealed this

First Day of August, 1995

*Attest:*

BRUCE LEHMAN

*Attesting Officer*     *Commissioner of Patents and Trademarks*